US005696269A

United States Patent [19]
Franklin et al.

[11] Patent Number: 5,696,269
[45] Date of Patent: Dec. 9, 1997

[54] PROCESS FOR THE PREPARATION OF CHLORINATION DERIVATIVES OF PYRIDINE COMPOUNDS AND UTILIZATION OF BIS(TRICHLOROMETHYL) SULFONE IN THE PROCESS

[75] Inventors: James Franklin, Brussels; Francine Janssens, Vilvoorde, both of Belgium

[73] Assignee: Reilly Chemicals S.A., Brussels, Belgium

[21] Appl. No.: 13,255

[22] Filed: Feb. 3, 1993

Related U.S. Application Data

[63] Continuation of Ser. No. 866,970, Apr. 7, 1992, abandoned, which is a continuation of Ser. No. 702,361, May 15, 1991, abandoned, which is a continuation of Ser. No. 353,959, May 18, 1989, abandoned.

[30] Foreign Application Priority Data

Jul. 15, 1988 [FR] France .................. 88 09718

[51] Int. Cl.$^6$ .................................. C07D 213/61
[52] U.S. Cl. .................................. 546/345
[58] Field of Search .................................. 546/345

[56] References Cited

U.S. PATENT DOCUMENTS 4,804,763  2/1989  Franklin .................. 546/345

OTHER PUBLICATIONS

Klingsberg, Erwin; *Pyridine and Its Derivatives, part one*, Interscience, New York, 1960, pp. 2–3.
Dorrepaal, W; "Halogenation of Aromatics . . . " *Chemical Abstracts* 75(13): 87828 w, Sep. 1971.

*Primary Examiner*—Jacqueline Haley
*Attorney, Agent, or Firm*—Woodard, Emhardt, Naughton, Moriarty & McNett

[57] ABSTRACT

The invention concerns a process for the preparation of chlorinated derivatives of pyridine compounds by a chlorination reaction of the corresponding pyridine compounds with molecular chlorine, carried out in the gaseous phase by means of bis(trichloromethyl)sulfone as a free radical initiator.

The obtained chlorinated derivatives of pyridine compounds, such as 2,6-dichloropyridine, can be used as chemical intermediates.

5 Claims, No Drawings

PROCESS FOR THE PREPARATION OF CHLORINATION DERIVATIVES OF PYRIDINE COMPOUNDS AND UTILIZATION OF BIS(TRICHLOROMETHYL) SULFONE IN THE PROCESS

This application is a continuation of application Ser. No. 07/886,970, filed Apr. 7, 1992, now abandoned, which is a continuation of application Ser. No. 07/702,361, filed May 15, 1991, now abandoned, which is a continuation of application Ser. No. 07/353,959, filed May 18, 1989 now abandoned.

The present invention concerns a process for preparing chlorinated derivatives of pyridine compounds, such as 2,6-dichloropyridine, from the corresponding pyridine compounds by means of molecular chlorine in the gaseous phase in the presence of bis(trichloromethyl)sulfone as a free radical initiator. The present invention also concerns the use of bis(trichloromethyl)sulfone as a free radical initiator.

To date, different techniques have been developed for the preparation of chlorinated derivatives of pyridine compounds; one of these techniques more particularly consists of the preparation of 2,6-dichloropyridine by a reaction of chlorination of pyridine by means of molecular chlorine. Upon improvements of these techniques, the processes can be divided into three major classes.

The first class comprises the so-called thermal procedures, carried out in a gaseous phase at a high temperature, generally above 350° C., and described particularly in U.S. Pat. No. 3,251,848 assigned to Dow. These procedures present various drawbacks, such as the very high temperatures needed and a significant formation of tars, which plug the reactor or pipes, thus making it difficult to execute the procedure continuously.

The second class of procedures comprises the procedures initiated by means of visible or ultraviolet radiations. Such procedures have been especially described in the document Chemical Abstract CA 84:164626u. Although these procedures allow the operation to take place at lower temperatures than do the thermal procedures, they present the drawback of leading to the formation of tarry by-products that soil the light tubes and subsequently decrease the initiation radiation, and thus the yield of the reaction. Furthermore, these procedures do not allow one to work at high pressure and require that the operation take place in reactors permeable to the initiation radiations, that is, reactors generally made of glass, which causes serious technological difficulties when the reactions are extrapolated to large industrial installations.

A third class of procedures comprises the so-called chemical procedures catalyzed by free radical initiators, as illustrated by the preparation of 2-chloropyridine, especially in patent application No. 0140438 in the name of Solvay & Cie., in which the free radical initiators used are organic peroxides such as ditertiary butyl peroxide.

The purpose of the present invention is to remedy the drawbacks of the known procedures. In particular, the procedure according to the invention leads to a high selectivity of 2,6-dichloropyridine and this at relatively low temperatures. The procedure also leads, for a given temperature, to a productivity superior to that obtained with the known procedures.

The procedure for a given temperature according to the invention presents an additional advantage over the known procedures: the initiation by-products and co-products are easily separated from the pyridine compounds and technical problems do not arise.

To this end, the invention concerns a procedure for the preparation of chlorinated derivatives of pyridine compounds by a substitutive chlorination reaction of the corresponding pyridine compounds by means of molecular chlorine in the gaseous phase and in the presence of a free radical initiator, in which the free radical initiator used is bis(trichloromethyl)sulfone.

By chlorination reaction carried out in the vapor phase, we mean a chlorination reaction carried out under temperature and pressure conditions such that all of the reactants, additives, catalysts, and products emitted from the reaction are in the vapor state in the reaction environment.

When the operation is performed at atmospheric pressure, these conditions are fulfilled for temperatures above 175° C. Good results have been obtained at temperatures between 200° and 300° C. and, more particularly, between 220° and 275° C.

The quantity of bis(trichloromethyl)sulfone used in the procedure according to the invention is generally less in relation to the known initiators. Generally, 0.01 to 10 mole percent of bis(trichloromethyl)sulfone is used, calculated in relation to the pyridine used. The preferred amounts are between 0.1 and 7.5 mole percent with relation to the pyridine, and amounts between 0.7 and 6 molar percent with relation to the pyridine are particularly preferred.

The molecular chlorine and the pyridine are usually used in mole ratios comprised between 0.1 and 25 moles of chlorine per mole of pyridine. Preferably, 0.5 to 15 moles of chlorine per mole of pyridine are used, most preferably 0.7 to 5 moles of chlorine per mole of pyridine.

By chlorinated derivatives of pyridine compounds, we mean all of the compounds comprising a six-atom heterocycle that carries a nitrogen heteroatom and is or is not substituted by one or several chlorine atoms; the heterocycle may carry one or several side chains such as, especially, alkyl chains with 1 to 5 atoms. Usually, the procedure of the invention is applied for the preparation of derivatives of pyridine or 3-methylpyridine (β-picoline). Preferably, the procedure of the invention is applied to the substitution of two hydrogen atoms by two chlorine atoms.

The procedure of the invention is applied most preferably for the preparation of 2,6-dichloropyridine.

In addition to the already mentioned reactants and initiators, one can use in the procedure according to the invention additives or diluents such as water vapor, nitrogen, and/or other gases that do not participate in the chlorination reaction itself or initiators that intervene in the chlorination reaction. As additives, halogenated derivatives of aliphatic compounds such as carbon tetrachloride, or inorganic products such as hydrogen chloride, nitrogen, or water vapor are preferably used.

The operation is preferably carried out with carbon tetrachloride.

In general, the halogenated organic diluents are added to the reaction medium in a ratio of 1 to 25 moles per mole of pyridine compound. When carbon tetrachloride is used as an organic additive, the preferred amounts are between 1.5 and 15 moles per mole of the pyridine compound.

The pressure at which the procedure according to the invention is carried out is usually between 1 and 10 bars; good results have been obtained at atmospheric pressure.

The residence time of the reactants in the reactor is generally between 1 and 30 sec, preferably between 2 and 20 sec.

The procedure according to the invention can be carried out in any apparatus or reactor that meets the operating conditions described above.

The chlorinated derivatives of the pyridine compounds obtained according to the procedure of the invention can be used in all known applications of these products, that is, as a chemical intermediate, especially for the manufacture of products intended for agriculture, cosmetics, and pharmaceutical products.

The chlorination reaction of the pyridine compounds can be applied to other aromatic heterocyclic compounds, on the condition, of course, that evident technical adjustments proper to the different products concerned are made.

The following examples serve to illustrate the invention.

EXAMPLE 1

Pyridine chlorination in the gaseous phase was carried out at 250° C. at atmospheric pressure in a spherical pyrex continous reactor-mixer automatically stirred by gas jets, and which measured about 1 $dm^3$ (Chem. Eng. Sc., 1973, 28, pp. 129–137); the reactants were introduced in gaseous form by means of a four-port injector placed in the middle of the sphere.

The reactor is placed in an enclosure, inside of which the air is electrically heated and stirred by means of a turbine to maintain the desired reaction temperature. The pyridine-water mixture is fed via an electrically heated vertical tubular evaporator. The carbon tetrachloride ($CCl_4$) is fed via a second, identical evaporator. The gaseous chlorine is injected into the bottom of the $CCl_4$ evaporator. The initiator is added in liquid form, in solution in the $CCl_4$, by a bypass giving into the introduction pipe of the gaseous $CCl_4+Cl_2$ mixture. The chlorination products leave the reactor through a tube diametrically opposite the introduction; then they are condensed and treated with aqueous NaOH to neutralize the residual chlorine and the formed HCl. After decantation, the organic phase is separated from the gaseous phase; the latter is subjected to extraction by means of chloroform, and the organic phase as well as the chloroform extract are analyzed by gas-phase chromatography. The total nitrogen in the extracted aqueous phase is determined by Kjeldahl's method.

Two moles of carbon tetrachloride, 0.05 mole of bis (trichloromethyl)sulfone, 1 mole of pyridine, and 1 mole of water are placed in this reactor. In addition, 4 moles of gaseous molecular chlorine are continuously injected. The operation takes place at atmospheric pressure. After the activation, a mixture of liquid having the following composition (per mole of pyridine used) is collected continuously:

| | |
|---|---|
| Monochloropyridines | 0.06 mole |
| Dichloropyridines (except 2,6-dichloropyridine) | 0.01 mole |
| Trichloropyridines | 0.15 mole |
| 2,6-Dichloropyridine | 0.78 mole |
| Pyridine | <0.005 mole |

The degree of conversion of the pyridine is close to 100%.

The residence time of the reactants in the reactor is 5 sec; the selectivity of 2,6-dichloropyridine is 78 mole percent.

EXAMPLE 2R

One operates as described in Example 1, but di-t-butyl peroxide is used as an initiator instead of bis (trichloromethyl)sulfone; all of the other parameters and conditions are identical to those described in Example 1.

The results are the following:

| | |
|---|---|
| Monochloropyridines | 0.58 mole |
| Dichloropyridines (except 2,6-dichloropyridine) | 0.01 mole |
| Trichloropyridines | 0.01 mole |
| 2,6-Dichloropyridine | 0.10 mole |
| Pyridine | 0.30 mole |

The degree of conversion of the pyridine is 70%.

The residence time of the reactants in the reactor is 10 sec; the yield of 2,6-dichloropyridine is 14 mole percent.

EXAMPLE 3R

One operates as described in Example 1, but without an initiator, and at 270° C.

The results are the following:

| | |
|---|---|
| Monochloropyridines | 0.27 mole |
| Dichloropyridines (except 2,6-dichloropyridine) | 0.01 mole |
| Trichloropyridines | 0.01 mole |
| 2,6-Dichloropyridine | 0.06 mole |
| Pyridine | 0.65 mole |

The degree of conversion of the pyridine is 35%.

The residence time of the reactants in the reactor is 10 sec; the yield of 2,6-dichloropyridine is 17 mole percent.

EXAMPLES 4 and 5

One operates as described in Example 1, but with initiators in the quantities presented in Table I. The observed results are also presented in Table I.

TABLE I

| | Example 4 | Example 5 |
|---|---|---|
| Initiator | | |
| Bis (trichloromethyl) sulfone moles per mole of pyridine | 0.02 | 0.01 |
| Results | | |
| Collected products, moles/mole of pyridine used | | |
| Monochloropyridines | 0.07 | 0.15 |
| Dichloropyridines (except 2,6-dichloropyridine) | 0.01 | 0.02 |
| Trichloropyridines | 0.11 | 0.06 |
| 2,6-Dichloropyridine | 0.81 | 0.76 |
| Pyridine | 0 | 0.01 |
| Balance | | |
| Residence time, seconds | 5 | 5 |
| Selectivity of 2,6-dichloropyridine, mole percent | 80 | 77 |
| Rate of conversion of pyridine, % | 100 | 99 |

We claim:

1. Process for the preparation of 2,6-dichloropyridine by a substitutive chlorination reaction of pyridine by means of molecular chlorine in the presence of a free radical initiator in the gaseous phase, characterized in that the free radical initiator used is bis(trichloromethyl)sulfone.

2. Process according to claim 1, characterized in that bis(trichloromethyl)sulfone is used in a ratio of 0.1 to 7.5 mole percent, calculated in relation to the pyridine.

3. Process according to claim 1 or claim 2, characterized in that the temperature at which the chlorination reaction takes place is between 200° and 300° C.

4. Process according to claim 1 or claim 2 characterized in that the chlorine is used in an initial mole ratio between 0.1 and 25 moles of chlorine per mole of pyridine.

5. Process according to claim 1 or claim 2 characterized in that the chlorination reaction is carried out in the presence of carbon tetrachloride.

* * * * *